United States Patent [19]
Chenite et al.

[11] Patent Number: 5,858,531
[45] Date of Patent: Jan. 12, 1999

[54] METHOD FOR PREPARATION OF POLYMER MICROPARTICLES FREE OF ORGANIC SOLVENT TRACES

[75] Inventors: Abdellatif Chenite, Kirkland; Amine Selmani, Laval, both of Canada

[73] Assignee: Bio Syntech, Chomedey, Canada

[21] Appl. No.: 736,421

[22] Filed: Oct. 24, 1996

[51] Int. Cl.$^6$ .............. B29B 9/10; B32B 27/36; B01J 13/04

[52] U.S. Cl. .............. 428/402; 264/4.4; 264/5; 264/7; 264/9; 424/425; 424/486; 428/402.24; 514/963

[58] Field of Search .............. 252/303; 264/46, 264/5, 7, 4.4, 9; 428/402, 402.24; 526/902; 528/361

[56] References Cited

U.S. PATENT DOCUMENTS

| | | |
|---|---|---|
| 2,976,574 | 3/1961 | Keutgen et al. . |
| 3,586,654 | 6/1971 | Lerman et al. ............ 264/5 X |
| 3,755,558 | 8/1973 | Scribner .................... 424/47 |
| 3,966,655 | 6/1976 | Kovacs et al. ............ 428/402 X |
| 4,454,198 | 6/1984 | Fickel et al. .............. 428/402 |
| 4,568,559 | 2/1986 | Nuwayser et al. ........ 428/402.24 X |
| 4,861,627 | 8/1989 | Mathiowitz et al. ...... 264/4.6 X |
| 4,902,792 | 2/1990 | Okuma et al. ............ 428/402 X |
| 4,933,105 | 6/1990 | Fong ........................ 264/4.6 X |

FOREIGN PATENT DOCUMENTS

PCT/FR93/
00576   6/1992   WIPO .

OTHER PUBLICATIONS

Rembaum A. and Toke Z. A., Eds., *Microspheres: Medical and Biological Applications*, CRC Press, Boca Raton, FL, 1988; Title Page and Table of Contents.

Mosbach K., 1988, Methods Enzymol., 137: 433.

Arshady R. 1993, Biomaterials, 14:5.

Jalil R. and Nixon J.R., 1990, *J. Microencapsul.*, 7:297.

Bodmeier R. and McGinity J.W., 1987, *J. Microencapsul.*, 4:279).

Pitt, C.G., *Biodegradable Polymers as Drug Delivery Systems,* Eds R. Langer and M. Chasin, Marcel Dekker, New York, NY, USA 1970, pp. 71–120).

Potts, J.E., Clendinning, R.A. and Cohen, S., 1975, *Soc. Plast. Eng. Thec. Pap.*, 21: 567–569.

*Primary Examiner*—Richard D. Lovering
*Attorney, Agent, or Firm*—Klauber & Jackson

[57] ABSTRACT

The present invention relates to a new method for the production of polymer microparticles. The method is carried out in the absence of organic solvent, and consists in the steps of (a) combining first and second polymers, the first and second polymers being immiscible, (b) heating the combination obtained in step (a) so as to melt the first and second polymers; (c) stirring the melted polymers obtained in step (b) under conditions effective to produce a biphasic system comprising a dispersed phase consisting of a dispersion of the first polymer and a matrix continuous phase comprising the second polymer, the dispersed phase containing microparticles of the first polymer dispersed in the matrix continuous phase; (d) solidifying the biphasic system obtained in step (c) so as to keep the microparticles of the first polymer dispersed in the matrix continuous phase; and (e) separating and isolating the microparticles of the first polymer from the matrix continuous phase, wherein the first polymer forming said dispersed phase is water-insoluble, while the second polymer forming the continuous phase is water-soluble.

13 Claims, 4 Drawing Sheets

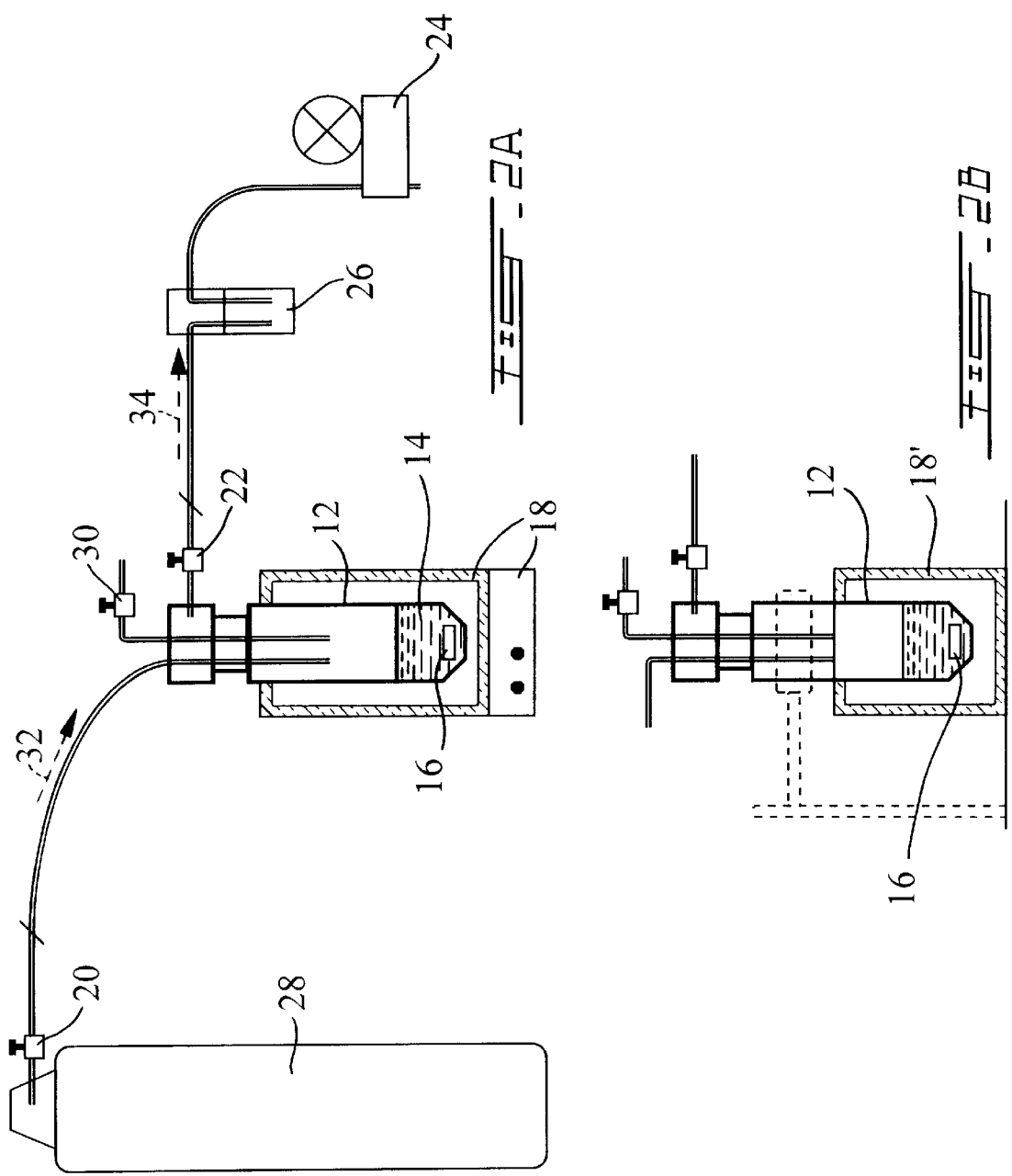

METHOD FOR PREPARATION OF POLYMER MICROPARTICLES FREE OF ORGANIC SOLVENT TRACES

BACKGROUND OF THE INVENTION (a) Field of the Invention

The invention relates to a method of preparation of polymer microparticles free of organic solvent traces.

(b) Description of Prior Art

There is a substantial interest in the preparation of polymer microparticles in the micrometer and submicrometer ranges, because of their potential applications. These kind of particles are produced by various manufacturing processes including suspension, emulsion and dispersion polymerization in addition to the well known solvent evaporation-based method. In the biotechnological field, polymer microparticles have attracted increasing attention as carrier matrices in a wide variety of applications, namely affinity chromatography, immobilization technologies, drug delivery systems, nuclear imaging and cell culturing (Rembaum A. and Toke Z. A., Eds., *Microspheres: Medical and Biological Applications*, CRC Press, Boca Raton, Fla., 1988; Mosbach K., 1988, *Methods Enzymol.*, 137:443; Arshady R., 1993, *Biomaterials*, 14:5).

Up to now, all methods reported that the fabrication of such microparticles requires a solution media, since they necessarily involve preliminary dissolution of polymers or relative monomers depending on the technique.

Aliphatic polyesters are preferred polymers for the preparation of biodegradable microparticles as devices for drug delivery and cell culturing. Such a preparation is often carried out in presence of $CH_2Cl_2$ or $CH_3Cl$ as organic solvent, and poly(vinyl alcohol), PVA, as surfactant. Accordingly, one cannot underestimate the toxicity risks associated with the solvent and surfactant residues remaining adsorbed on the microparticles inner and outer surfaces. The surfactant problem may be solved by using other surfactants, such as methyl cellulose or poly(ethylene oxide) Sorbitan™ monoalkaneoates (Tween™) instead of PVA (U.S. Pat. No. 4,933,105 in the name of Fong J. W.; Jalil R. and Nixon J. R., 1990, *J. Microencapsul.*, 7:297; Bodmeier R. and McGinity J. W., 1987, *J. Microencapsul.*, 4:279).

More recent patent gets around the surfactant problem by using PLA or PLGA oligomer to prepare microparticles of PLA and PLGA polymers (Vert M. et al., International Patent Application published under No. WO93/25191 on Dec. 23, 1993). However, the solvent problem seems to be too difficult to overcome, and thus its use remains an important drawback of the prior art method.

Both mentioned patents are based on solvent-evaporation method to produce microparticles of PLA or PLGA as matrices for drugs or cells. The employed method consists to dissolve desired polymer in $CH_2Cl_2$ or $CH_3Cl$, after which the resultant solution is emulsified in aqueous media containing a surfactant as stabilizing agent for the dispersed phase. Once the emulsion is formed the organic solvent is taken off by simple evaporation. The first patent uses Na-Oleate as surfactant, while in the second one, the microparticles are prepared in presence of PLA and PLGA oligomers, which allowed them to be considered surfactant-free.

It would be highly desirable to be provided with an alternative method aiming to produce microparticles from melted polymers, which avoid using organic solvents which are mostly toxic. Such a method is expected to receive a particular attention in biotechnological field.

SUMMARY OF THE INVENTION

Most polymer microparticles of the present invention are often intended to be administered to the patients by an injection or as an implant for medical and pharmaceutical applications. Therefore, the health considerations require that the method of the present invention lead to the production of polymer microparticles completely free of risk or free from any suspicious toxic substance. This constitutes a real challenge because of the problems associated with the known synthetic method, which always requires a preliminary dissolution of polymer in an organic solvent, and there exists no drying processing capable to remove all solvent traces.

One aim of the present invention is to provide an alternative method for the production of microparticles from melted polymers, which avoid the use of organic solvents which are mostly toxic.

Another aim of the present invention is to provide polymer microparticles free of toxic organic solvent traces.

Third aim of the present invention is to avoid the toxicity risks of residual surfactant by using poly(ethylene glycol), which has been evaluated biocompatible and non toxic material.

In accordance with the present invention there is provided a method for the production of polymer microparticles free of organic solvent traces, a polymer microparticle produced by the method and the use thereof. The invention further provides a method for the production of microparticles, wherein the method uses non-toxic surfactant such as preferably poly(ethylene glycol) as a second polymer, thereby producing microsphere or microparticle free of solvent traces.

BRIEF DESCRIPTION OF THE DRAWINGS

FIGS. 2A and 2B illustrate a set up for the method in accordance with one embodiment of the present invention.

DETAILED DESCRIPTION OF THE INVENTION

In accordance with one embodiment of the present invention, there is provided a new method for the production of polymer microparticles, which method is carried out in the absence of organic solvent, and comprising the following steps:

(a) combining first and second polymers, the first and second polymers being immiscible;

(b) heating the combination obtained in step (a) so as to melt the first and second polymers;

(c) subjecting the melted polymers obtained in step (b) to deformation in a mixing device, under conditions effective to produce a biphasic system, the biphasic system comprising a dispersed phase and a matrix continuous phase, the dispersed phase consisting of a dispersion of the first polymer, the matrix continuous phase comprising the second polymer, the dispersed phase comprising microparticles of the first polymer dispersed in the matrix continuous phase;

(d) solidifying the biphasic system obtained in step (c) so as to keep the microparticles of the first polymer dispersed in the matrix continuous phase; and (e) separating and isolating the microparticles of the first polymer from the matrix continuous phase, wherein the first polymer forming the dispersed phase is water-insoluble.

In another embodiment of the method of the present invention, the heating in step (b) is performed under vacuum or inert gas atmospheres.

In another embodiment of the method of the present invention, the first polymer is water-insoluble and the second polymer is water-soluble.

The solidifying of step (d) may be carried out by cooling down the biphasic system in ice-cold water, in liquid nitrogen or any other method known in the art.

In another embodiment of the method of the present invention step (e) is carried out by solubilizing the matrix followed by filtration or decantation thereof. The method may further comprise the steps of washing and drying the microparticles. The dispersed phase may consist of spherical droplets, microspheres, platelets or fibrils.

In accordance with the present invention, there is provided a microparticle free of organic solvent traces. Such a microparticle may be shaped as spheroids, ellipsoids (deformed microspheres), platelets, fibrils.

The microparticles of the present invention may be used as a carrier matrix. Such a microparticle has a given resistance to water or enzymes and is used in pharmaceuticals as a matrix carrier for controlled drug delivery.

The microparticles of the present invention may be used in preparing a coating pre-formed polymer/drug system to form a double-walled microcapsules. An encapsulated drug or bioactive agent is coated with the microparticle produced in accordance with the method of the present invention. This provides an improved system for drug delivery for preventing a "burst-effect" of the microcapsules, thereby allowing a better control release of drug.

Figure 1A:
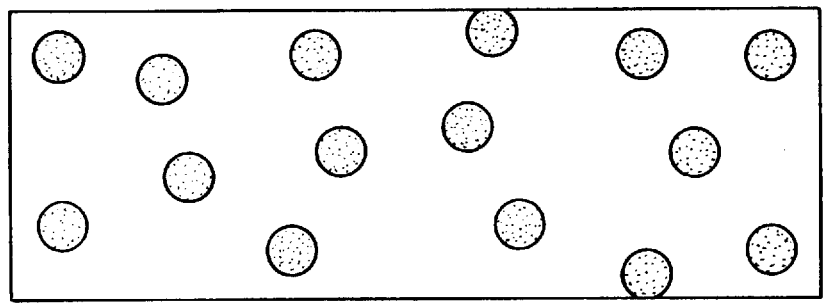
FIGS. 1A to 1C illustrate different types of dispersion of polymers A (black) in the matrix of an immiscible polymer B (white)
Figure 1B:
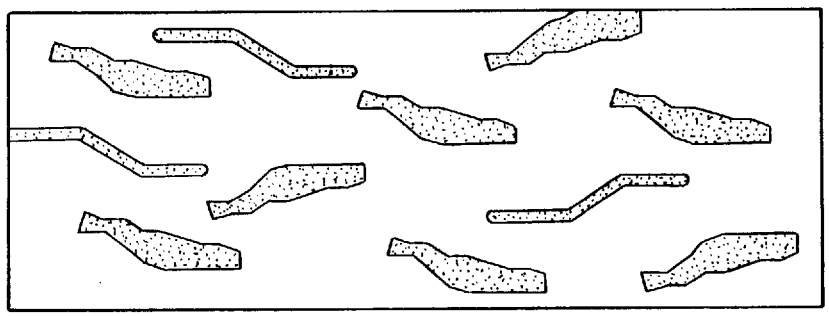
Figure 1C:
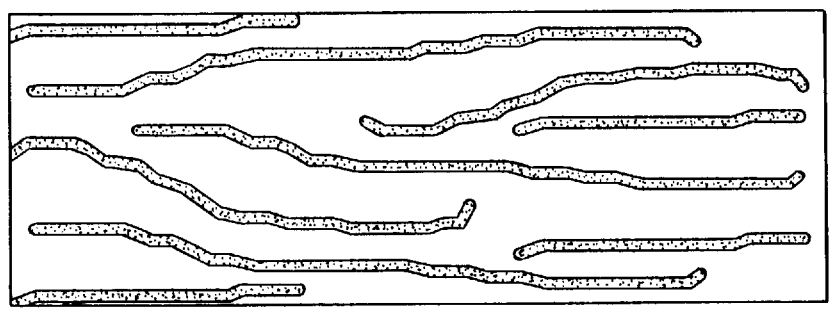

Combining two incompatible or immiscible polymers may lead to a biphasic system consisting of a first polymer dispersed in a matrix formed by a second polymer. The dispersed phase may take the form of spheres (FIG. 1A), biaxial platelets (FIG. 1B) or one dimensional fibrils (FIG. 1C), among other forms. It is possible that the microspheres or spherical droplets are then progressively extended to platelets or fibrils by deformation. The dispersed phase of polymer may also take an oval form among other forms.

In accordance with the present invention, the first polymer include, without limitation, any one of the following polymers:

poly(caprolactone), (PCL);
poly(lactic acid), (PLA);
poly(lactic-co-glycolic acid), (PLGA);
poly(3-hydroxybutyrate), (PHB);
poly(3-hydroxybutyrate-hydroxyvalerate), (PHB-HV);
poly(1,4, butylene adipate), (PBA);
poly(ethylene adipate)(PEA);
poly(styrene), (PS); and
poly(ethylene), (PE).

In accordance with the present invention, the second polymer include, without limitation, any one of the following oligomers:

poly(ethylene glycol), (PEG), with variable molecular weight ($M_w$=400 to 10000);
poly(propylene glycol), (PPG), with variable molecular weight ($M_w$=1000 to 3000); and
any other polymer having amphiphilic properties.

Polymers with low molecular weight, or oligomers, proved useful as matrices because they provide relatively low viscosity with respect to the polymers with high molecular weight.

The polymers with a relatively high melting temperature (higher than 120° C.) must be used under inert or vacuum conditions in accordance with the present invention.

The morphology of immiscible polymer mixture depends on the interfacial tension between the phases, the viscosity and the elasticity. The polymer occupying the most space tends to assume the role of the continuous phase. The shape and the size of the dispersed phase are determined by the drop breakup and coalescence, which in turn are governed by the deformation field imposed by the mixing device, interfacial tension and rheological characteristics of both polymers.

The polymer with the lower viscosity tends to encapsulate the more viscous polymer during the mixing, since mixing reduces the rate of energy dissipation. Thus, the viscosity may be offset by the proportions of the polymers to control which phase is continuous.

In accordance with one embodiment of the present invention, the method essentially consists in forming a melt dispersion of desired water-insoluble polymer in melted water-soluble polymer.

FIGS. 2A and 2B illustrate a set up of the apparatus 10 used in order to carry out the method of preparation of polymer in accordance with one embodiment of the present invention.

To prevent polymers from eventual degradation upon heating (18, 18'), both melted polymers 14 (polymer A+polymer B) are mixed with a stirring bar 16 under vacuum 34 or inert gas atmosphere 32 ($N_2$ or Ar).

In a first stage, the mixing, heating and homogenization of the polymer mixture is performed using the equipment described in FIG. 2A. Polymer A and polymer B (14) are introduced through the inlet and valve (30) in the heat-resistant flask (12) and mixed by using magnetic stirrer (16). Heating of the polymer mixture in the flask is ensured by the insulated heater/temperature control (18) and performed under inert atmosphere. Gas ($N_2$ or Ar) is introduced from the bottle (28) via the valve (20) in the flask (inert gas flow 32). The low pressure in the flask is obtained by pumping (vacuum 34) through the vacuum pump (24), the vacuum trap (26) and the valve (22). Inert gas flow (32) and vacuum flow (34) can be activated simultaneously or independently.

In a second stage FIG. 2B, the polymer mixture (14) in the heat-resistant flask (12) is disconnected from the gas flow and vacuum circuits (valves 20 and 22) and pulled out from the heated system and insulated envelope (18). It is rapidly cooled in a cooling bath/temperature controlled (18') and maintained in position at low temperature. All heated/cooled envelopes and controls are equipped with high-precision thermometers.

All parent systems enabling the controlled mixture of two polymers at high temperature under gas atmosphere and vacuum and the fast cooling of this polymer mixture can be used for processing polymer microparticles or microspheres without any traces of organic solvent, with no restriction.

The melt mixture is frozen in ice water (about 4° C.), in dry ice (about −40° C.) or in liquid nitrogen, in order to keep the particles of desired polymer dispersed in polymer matrix. The dispersed polymer is then separated from the mixture by simple dissolution of the matrix in water, which should not dissolve the dispersed phase. The microparticles are then recovered by simple filtration, washed and dried in air or under vacuum.

Mixture compositions ranging from 1 to 10% were used. Typical experiments were carried out to prepare microparticles from melted Poly(caprolactone), Poly(1,4 butylene adipate), PBA and Poly(styrene), PS. Poly(caprolactone), PCL, was used in an amount of about (0.252 g) with Poly(ethylene glycol), PEG (1000) in an amount of about (10.0 g). Poly(1,4 butylene adipate), PBA, was used in an amount of about (0.200 g) with Poly(ethylene glycol), PEG (400) in an amount of about (10.0 g). Poly(styrene), PS, was used in an amount of about (0.160 g) with Poly(propylene glycol), PPG (1000) in an amount of about (10.0 g). The temperature used are indicated in Table I below.

TABLE 1

| Involved polymers | | |
|---|---|---|
| Polymer | Matrix | Temperature °C. |
| PCL | PEG (1000) | 70 |
| PBA | PEG (400) | 70 |
| PS | PEG (1000) | 240 |

The present invention will be more readily understood by referring to the following examples which are given to illustrate the invention rather than to limit its scope.

EXAMPLE I

PCL microparticle

Poly(caprolactone), PCL, is an ideal polymer of potential applications reserved to this method. PCL is an aliphatic polyester that has been intensively investigated as potential biomaterial (Pitt, C. G., *Biodegradable Polymers as Drug Delivery Systems*, Eds R. Langer and M. Chasin, Marcel Dekker, New York, N.Y., U.S.A. 1970, PP. 71–120). It has been evaluated as biodegradable packing material (Potts, J. E., Clendinning, R. A. and Cohen, S., 1975, *Soc. Plast. Eng. Thec. Pap.*, 21: 567–569) and as long-term implantable systems, to deliver drugs or cells (i.e. Capronor™, a one-year implantable contraceptive device). On the basis of a large number of tests PCL as well as Caprolactone are presently regarded as non-toxic and tissue compatible materials. Consequently, the Capronor™ system has been undergoing U.S. Food and Drug Administration (FDA) approval for phase I and phase II clinical trials.

Figure 3A:
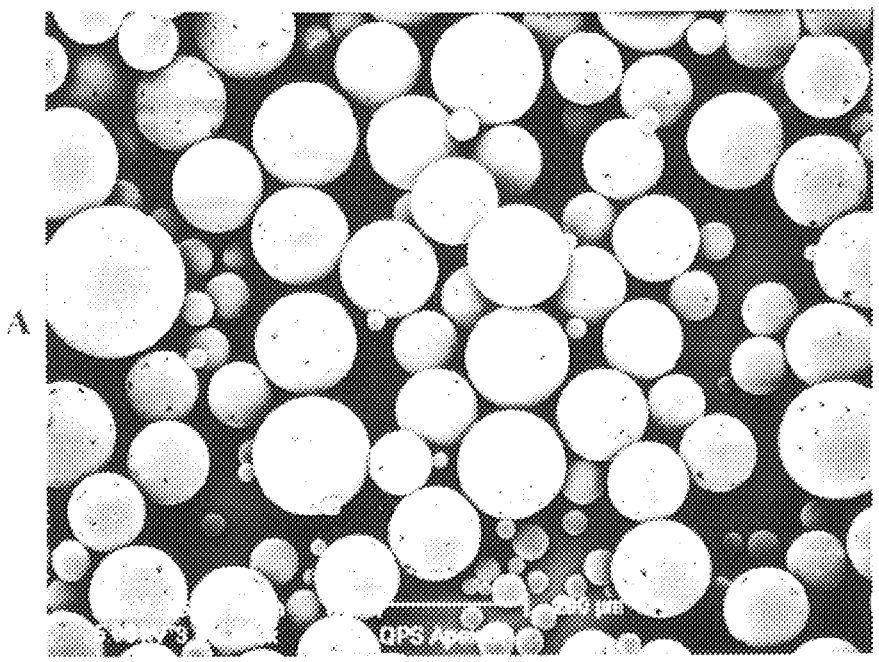
FIGS. 3A to 3C illustrate microparticle in accordance with one embodiment of the present invention.
Figure 3B:
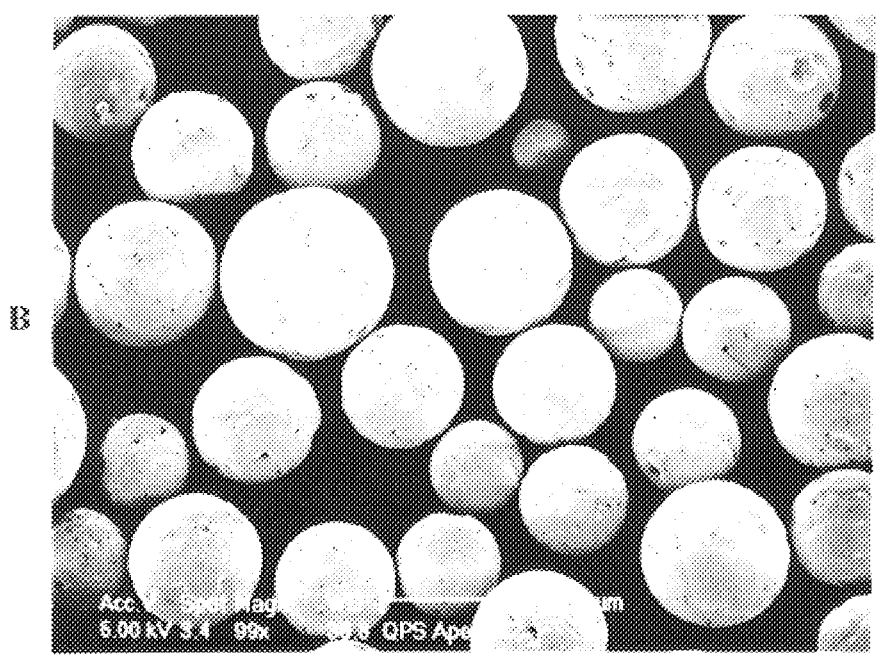
Figure 3C:
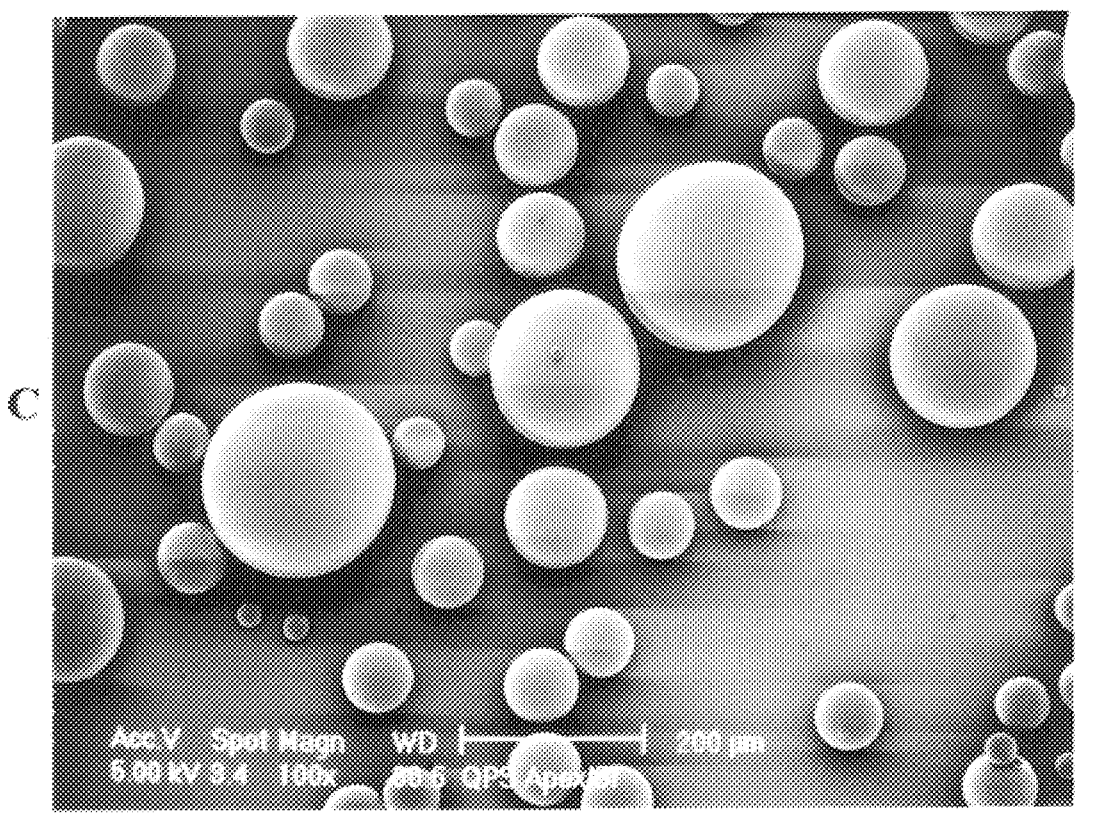

The spherical shape of microparticles, has been evidenced by scanning electron microscopy. FIG. 3 shows SEM micrographs of typical polymer microparticles, prepared along with the present method, for PCL (FIG. 3A), PBA (FIG. 3B) and PS (FIG. 3C) respectively. In all cases, particles appeared well separated and perfectly spherical. Surfaces were smooth for PS and, more or less rough for PCL and PBA microparticles. This is probably due to the difference of intrinsic viscosity of polymers, and to the interfacial tensions between the matrix and the dispersed phases. Each batch of microparticles showed a wide size distribution, with diameters varying from 20 to 200 μm. However, most of particles had approximate diameters ranging from 50 to 150 μm for PCL (FIG. 3A), 100 to 180 μm for PBA (FIG. 3B) and 50 to 120 μm for PS (FIG. 3C). The particle sizes also depend on the composition and the cooling rate in addition to the polymer characteristics and the stirring forces.

The present invention can also provide a method for coating pre-formed or polymer/drug matrix to form a double-walled microcapsules. Thus, microcapsules of PLA, PLGA, P(HB-HV), etc. with drug or bioactive agent can be coated with PCL, providing an improved system for drug delivery, which can prevent the so-called "burst-effect" and allows a better controlled release of drug. This double-walled microcapsule may find an important role in the preparation and formulation of controlled, slow-released drugs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A new method for the production of polymer microparticles, said method is carried out in the absence of organic solvent, and comprising the following steps:
    (a) combining first and second polymers, said first and second polymers being incompatible or immiscible;
    (b) heating the combination in step (a) so as to melt the first and second polymers;
    (c) subjecting the melted polymers obtained in step (b) to deformation in a mixing device, under conditions effective to produce a biphasic system, said biphasic system comprising a dispersed phase and a matrix continuous phase, said dispersed phase consisting of a dispersion of the first polymer, said matrix continuous phase comprising the second polymer, said dispersed phase containing microparticles of the first polymer dispersed in said matrix continuous phase;
    (d) solidifying the biphasic system obtained in step (c) so as to keep the microparticles of the first polymer dispersed in the matrix continuous phase; and
    (e) separating and isolating the microparticles of the first polymer from the matrix continuous phase,
wherein the first polymer in said dispersed phase is less water-soluble than the second polymer.

2. The method of claim 1, wherein heating in step (b) is performed under vacuum or inert gas atmospheres.

3. The method of claim 1, wherein the first polymer is water-insoluble and the second polymer is water-soluble.

4. The method of claim 1, wherein solidifying in of step (d) is carried out by cooling down the biphasic system in ice-cold water or in liquid nitrogen.

5. The method of claim 1, wherein step (e) is carried out by solubilizing the matrix followed by filtration or decantation thereof to isolate the microparticles of the first polymer.

6. The method of claim 5, further comprising the steps of washing and drying the microparticles.

7. The method of claim 1, wherein the dispersed phase consists of spheroid, ellipsoid, platelet or fibril microparticles.

8. The method of claim 1, wherein the first polymer is selected from the group consisting of:
    poly(caprolactone) (PCL);
    poly(lactic acid) (PLA);
    poly(lactic-co-glycolic acid) (PLGA);
    poly(3-hydroxybutyrate) (PHB);
    poly(3-hydroxybutyrate-hydroxyvalerate) (PHB-HV);
    Poly(1,4-butylene adipate) (PBA);
    Poly(ethylene adipate) (PEA);
    poly(styrene) (PS); and
    poly(ethylene) (PE).

9. The method of claim 1, wherein the second polymer is selected from the group consisting of:

poly(ethylene glycol) (PEG), having a molecular weight varying from 400 to 10000; and poly(propylene glycol) (PPG) having a molecular weight varying from 1000 to 3000.

10. A microparticle free of organic solvent traces produced by the method of claim 1.

11. The microparticle of claim 10 wherein said microparticle is shaped as a microsphere, a spherical droplet, a platelet, a fibril or an ellipsoid.

12. A method for the production of polymer microparticles, said method being carried out in the absence of organic solvent and comprising the following steps:

(a) combining the first and second polymers, said first and second polymers being incompatible or immiscible;

(b) heating the combination obtained from (a) under vacuum or inert gas atmospheres so as to melt the first and second polymers;

(c) shaking the melted polymers obtained in step (b) under conditions effective to produce a biphasic system, said biphasic system comprising a dispersed phase and a matrix continuous phase, said dispersed phase consisting of a dispersion of the first polymer, said matrix continuous phase comprising the second polymer, said dispersed phase containing microparticles of the first polymer in the shape of microspheres, platelets or fibrils;

(d) cooling down the biphasic system obtained in (c) so as to solidify same in order to keep the microparticles of the first polymer dispersed in the matrix;

(e) solubilizing the matrix with water;

(f) filtering or decantating the solubilized matrix;

(g) washing the microparticles; and (h) drying said microparticles, wherein the first polymer in said dispersed phase is selected from the group consisting of:

poly(caprolactone) (PCL);

poly(lactic acid) (PLA);

poly(lactic-co-glycolic acid) (PLGA);

poly(3-hydroxybutyrate) (PHB);

poly(3-hydroxybutyrate-hydroxyvalerate) (PHB-HV);

poly(1,4-butylene adipate) (PBA);

poly(ethylene adipate) (PEA);

poly(styrene) (PS); and poly(ethylene) (PE), and the second polymer is selected from the group consisting of:

poly(ethylene glycol) (PEG), having a molecular weight varying from 400 to 10000; and poly(propylene glycol) (PPG) having a molecular weight varying from 1000 to 3000.

13. A microparticle free of organic solvent traces produced by the method of claim 12.

* * * * *

UNITED STATES PATENT AND TRADEMARK OFFICE
CERTIFICATE OF CORRECTION

PATENT NO. : 5,858,531
DATED : January 12, 1999
INVENTOR(S) : Abdellatif Chenite and Amine Selmani It is certified that error appears in the above-identified patent and that said Letters Patent is hereby corrected as shown below:

<u>Title page,</u>
Please delete the inventors and insert in their place:
-- Abdellatif Chenite, Kirkland; Cyril Chaput, Montréal; Amine Selmani, Laval, all of Canada --

Signed and Sealed this

Eighteenth Day of September, 2001

*Attest:*

*Nicholas P. Godici*

*Attesting Officer*

NICHOLAS P. GODICI
*Acting Director of the United States Patent and Trademark Office*